United States Patent [19]

Yamato et al.

[11] Patent Number: 4,683,220

[45] Date of Patent: Jul. 28, 1987

[54] NOVEL PHYSIOLOGICALLY ACTIVE SUBSTANCES K-26, A PROCESS FOR PREPARATION THEREOF AND A PHARMACEUTICAL COMPOSITION CONTAINING THE SAME

[75] Inventors: Masayuki Yamato, Machida; Hiroshi Kase, Koganei; Isao Kawamoto, Hiratsuka, all of Japan; Masaji Kasai, Rockville, Md.; Kunikatsu Shirahata, Komae, Japan; Takashi Deguchi, Mishima, Japan; Katsuichi Shuto, Shizuoka, Japan; Akira Karasawa, Shizuoka, Japan; Ryo Okachi, Shizuoka, Japan; Kiyoshi Nakayama, Sagamihara, Japan

[73] Assignee: Kyowa Hakko Kogyo Co., Ltd., Tokyo, Japan

[21] Appl. No.: 912,685

[22] Filed: Sep. 26, 1986

Related U.S. Application Data

[63] Continuation of Ser. No. 744,309, Jun. 13, 1985, abandoned, which is a continuation of Ser. No. 661,886, Oct. 18, 1984, abandoned, which is a continuation of Ser. No. 359,030, Mar. 17, 1982, abandoned.

[30] Foreign Application Priority Data

Mar. 20, 1981 [JP] Japan .................................. 56-40651

[51] Int. Cl.$^4$ ............................................ A61K 37/64
[52] U.S. Cl. ...................................................... 514/7

[58] Field of Search ............................ 530/330; 514/7

[56] References Cited

U.S. PATENT DOCUMENTS

| | | | |
|---|---|---|---|
| 4,016,148 | 4/1977 | Atherton et al. ................... | 424/177 |
| 4,100,275 | 7/1978 | Atherton et al. ................... | 424/271 |
| 4,127,649 | 11/1978 | Atherton et al. ................... | 424/271 |
| 4,134,972 | 1/1979 | Atherton et al. ................... | 424/271 |
| 4,213,969 | 7/1980 | Baylis ................................. | 424/177 |
| 4,250,085 | 2/1981 | Atherton et al. ............ | 260/112.5 R |
| 4,331,591 | 5/1982 | Baylis .......................... | 260/112.5 R |

FOREIGN PATENT DOCUMENTS 342192 3/1978 Austria .

OTHER PUBLICATIONS

Lehninger, *Biochemistry*, 2nd Ed., Warth Publishers, Inc. pp. 73–75, The Amino Acids Building Blocks of Proteins.
Yue et al. *Diabetes*, vol. 24, No. 7, 625–632 (1975).

*Primary Examiner*—Delbert R. Phillips
*Attorney, Agent, or Firm*—Fitzpatrick, Cella, Harper & Scinto

[57] ABSTRACT

Disclosed is a novel physiologically active substance, K-26, a process for preparation thereof and a pharmaceutical composition containing the same. The composition of matter, K-26, is useful as a hypotensive agent.

3 Claims, 4 Drawing Figures

NOVEL PHYSIOLOGICALLY ACTIVE SUBSTANCES K-26, A PROCESS FOR PREPARATION THEREOF AND A PHARMACEUTICAL COMPOSITION CONTAINING THE SAME

This application is a continuation of application Ser. No. 744,309, filed June 13, 1985 now abandoned which is a continuation of application Ser. No. 661,886, filed Oct. 18, 1984, now abandoned, which is a continuation of application Ser. No. 359,030, filed Mar. 17, 1982, now abandoned.

BACKGROUND OF THE INVENTION

The present invention relates to a novel physiological active substance, a process for producing the same and a pharmaceutical composition containing the same.

New physiologically active substances useful as medicaments or their intermediates are always in demand. To this end, it has been found that a new physiologically active substance exhibiting marked hypotensive activity is produced in a culture liquor of a microorganism belonging to the Actinomycetes. This substance has been tentatively named K-26, and its properties, a process for producing the same and a pharmaceutical composition containing the same are described hereinafter.

SUMMARY OF THE INVENTION

In accordance with the present invention, K-26 is produced by culturing a K-26 producing strain of microorganism belong to Actinomycetes in a nutrient medium until recoverable amounts of K-26 are formed in the culture liquor and isolating said K-26 therefrom.

In accordance with the composition of matter aspect of the present invention a novel physiologically active substance exhibiting hypotensive activity is represented by the formula

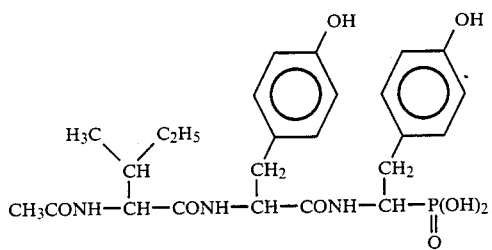

Finally, the present invention pertains to pharmaceutical hypotensive compositions containing an effective amount of the composition K-26 along with pharmacologically acceptable excipients.

DETAILED DESCRIPTION OF THE INVENTION

Figure 1:
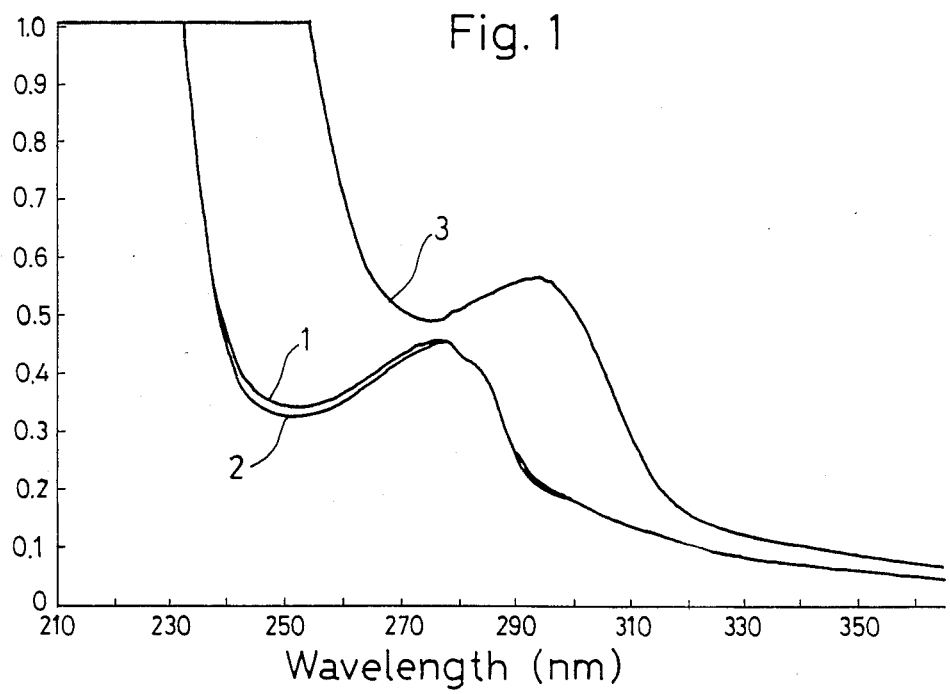
FIG. 1 is the ultraviolet absorption spectrum of K-26, wherein (1) is the results of measurement in a neutral state, (2) in an acid state, and (3) in an alkaline state.

For the production of the present physiologically active substance, microorganisms belonging to Actinomycetes are used. An example of suitable strains is a strain, hereinafter referred to as the K-26 strain, isolated by the present inventors from a soil sample from the bank at Kadoike in Numazu city in Shizuoka Prefecture, Japan. The morphological, cultural and physiological characteristics of this strain determined according to the procedure described by Searing et al in Intern. J. Syst. Bacteriol. 16 313–340 (1966) are as follows:

I. GROWTH ON VARIOUS CULTURE MEDIA

The growth and color characteristics when the K-26 strain is cultured on various culture media at 28° C. for 2 weeks are given below. The color identification is made in accordance with the color classification of "Color Harmony Manual" (Container Corporation of America).

(1) Sucrose-nitrate agar medium
  Growth: very poor
(2) Glucose-asparagine agar medium
  Growth: very poor
(3) Glycerol-asparagine agar medium (ISP No. 5)
  Growth: very poor
(4) Glycerol-calcium malate agar medium
  Growth: very poor
(5) Egg-albumin agar medium
  Growth: very poor
(6) Starch-inorganic salt agar medium (ISP No. 4)
  Growth: poor, smooth
  Reverse color: bright coral red (6 na)
  Aerial mycelium: none
  Soluble pigment: none
(7) Nutrient agar medium
  Growth: poor or moderate, granular
  Reverse color:
    bright shell pink (6 ea) to
    bright peach (5 ia)
  Aerial mycelium: none
  Soluble pigment: none
(8) Yeast extract-malt extract agar medium (ISP No. 2)
  Growth: poor or moderate, granular
  Reverse color: bright coral red (6 na) to tomato red (6½ pe)
  Aerial mycelium: none
  Soluble pigment: none
(9) Oatmeal agar medium (ISP No. 3)
  Growth: good, smooth
  Reverse color: chinese red (6 pc)
  Aerial mycelium: none
  Soluble pigment: none
(10) Glucose-yeast extract agar medium
  Growth: moderate or good, granular
  Reverse color: bright coral red (6 pa) to tomato red (6½ pa)
  Aerial mycelium: none
  Soluble pigment: none
(11) Bennet's agar medium
  Growth: moderate, granular
  Reverse color: apricot (4 ga) to chinese red (6 pd)
  Aerial mycelium: poor, white (a)
  Soluble pigment: none
(12) Emerson's agar medium
  Growth: poor or moderate
  Reverse color: bright coral red (6 pa)
  Aerial mycelium: none
  Soluble pigment: none
(13) Hickey-Tresnor's agar medium
  Growth: moderate, granular Reverse color: Light cherry red (6 la) to chinese red (6 pc)
Aerial mycelium: poor, white (a)
Soluble pigment: none
(14) Peptone-yeast extract-iron agar medium (ISP No. 6)
Growth: poor, smooth
Reverse color: peach (5 ga)
Aerial mycelium: none
Soluble pigment: none
(15) Tyrosine agar medium (ISP No. 7)
Growth: poor, smooth
Reverse color: fresh pink (5 ca) to bright orange (5 na)

II. PHYSIOLOGICAL PROPERTIES

To determine the physiological properties, the K-26 strain is cultured at 28° C. for 2 weeks except for the determination of optimum temperature and actions upon gelatin, milk and cellulose. The optimum temperature is determined after 5 days of culturing and actions upon milk, gelatin and cellulose are observed after culturing at 28° C. for 4 weeks. The present strain fails to grow on the inorganic medium (ISP No. 9) of Pridham-Gottlieb, and thus the test for utilization of a carbon source is carried out on the Ludemann's medium (N.Y. Acad. Sci. 33 207, 1971).

(1) Utilization of carbon source: D-xylose, D-glucose, D-fructose, D-galactose and starch are utilized. D-arabinose, inositol, L-rhamnose, glycerol, D-lactose and α-melibiose are not utilized. Raffinose, mannitol and mannose are slightly utilized.
(2) Liquefaction of gelatin: Negative
(3) Action upon milk: neither coagulation nor liquefaction
(4) Decomposition of cellulose: negative
(5) Hydrolysis of starch: positive
(6) Optimum growth pH: 6.5–7.8
(7) Optimum growth temperature: 28° C.–37° C.
(8) Formation of tyrosinase: negative
(9) Formation of melanoid pigment: negative

III. CELL WALL COMPOSITION

The cell wall of the K-26 strain contains the amino acids meso-diaminopimelic acid, alanine and glutamic acid, but neither LL-diaminopilmelic acid nor glycine are found. By analysis of sugars in the whole-cell according to the method of Lechevalier et al. (The Actinomycetales, Gustav Fister Verlag. Jena. 311–316, 1970), ribose, glucose, galactose, madurose and a small amount of mannose are detected, but neither arabinose nor xylose is detected. According to the Lechevalier et al. classification (Intern. J. System. Bacteriol. 20 435–443, 1970), the K-26 strain has cell walls of type III and a type B whole-cell sugar pattern.

IV. MORPHOLOGICAL PROPERTIES

The present strain grows poorly on a chemically defined medium such as sucrose-nitrate agar medium, glucose-asparagine agar medium, etc., but grows vigorously on a natural nutrient medium such as glucose-yeast extract agar medium, oatmeal agar medium, and the like. Its substrate mycelium is relatively long, branched and 0.4–0.6 μm in diameter. No fragmentation of mycelium is observed. The aerial mycelia formed on Bennet's agar medium or Hickey-Tresnor's agar medium are white and well developed, non-septated and 0.6–0.8 μm in diameter. The present strain fails to form spores and sporangium on the substrate mycelium and aerial mycelium so long as the media used are concerned. No formation of sclerotium is observed.

Since the present strain forms relatively long substrate mycelium and aerial mycelium with fine diameters, it is a strain belonging to Actinomycetes. Since the strain has the cell wall composition of type III and the whole-cell sugar pattern of type B, it may be classified into any of the genera Actinomadura, Microbispora, Streptosporangium, Spirillospora and Planomonospora, but the genus of the K-26 strain has not been identified because of the failure to observe spores and sporangium. The present strain has thus been deposited as a kind of Actinomycetes under FERM P-5889 in the Fermentation Research Institute of Agency of Industrial Science and Technology, Japan; and has also been deposited under NRRL 12379 in ARS culture collection, Peoria, Ill., United States of America. The present strain can be mutated by various mutational treatments such as ultraviolet irradiation, $Co^{60}$ irradiation, X-ray irradiation and treatment with various mutagents as is the case with other actinomycetes. All such strains having an ability to produce K-26, even though thus mutated, can be used in the present invention.

Ordinary procedures for culturing actinomycetes are used for culturing the present K-26 producing strains.

Either a synthetic medium or a natural medium may be used so long as it properly contains carbon source(s), nitrogen source(s), inorganic salt(s), etc. As the carbon source, glucose, starch, mannose, fructose, sucrose, molasses, etc. are used alone or in combination. Hydrocarbons, alcohols, organic acids, etc. can also be used, depending upon the assimilability of the microorganisms. As the nitrogen source, inorganic or organic nitrogen-containing compounds such as ammonium chloride, ammonium sulfate, urea, ammonium nitrate and sodium nitrate, and natural nitrogen sources such as peptone, meat extract, yeast extract, dry yeast, corn steep liquor, soybean meal, casamino acid and soluble vegetable protein are used alone or in combination. As inorganic salts, sodium chloride, potassium chloride, calcium carbonate, phosphate, etc. can be added to the medium. Organic or inorganic substances capable of promoting growth of the present strains or production of K-26 can be optionally added to the medium if desired.

A liquid culturing method, particularly a submerged stirring culture method, is most suitable for culturing the strains of the present invention. Culturing is preferably carried out at a temperature of 25°–40° C. and at a pH of around neutrality. K-26 is formed and accumulated in the culture liquor usually after 3–5 days of liquid culturing. When the accumulation in the culture liquor reaches a maximum, culturing is discontinued and the desired substance is isolated and purified from the filtrate of the culture liquor obtained by filtering off the cell bodies.

Ordinary procedures for isolating metabolic products of microorganisms from a culture liquor filtrate is used for isolation and purification of K-26. K-26 is a water-soluble, acidic substance as described hereinafter, and thus a procedure utilizing these properties is applied. That is, such procedures as adsorption and desorption by active carbon, Diaion HP-10 (adsorption resin made by Mitsubishi Kasei Kogyo Co., Ltd., Japan), etc., column chromatography by various anion exchange resins, cellulose column chromatography, silica gel column chromatography, QAE-Sephadex column chromatography, DEAE-Sephadex A-25 column chromatography, Sephadex LH-20 column chromatography (QAE-Sephadex, DEAE-Sephadex A-25 and Sephadex LH-20 are molecular sieves made by Pharmacia Fine Chemicals Inc., Sweden), etc, can be used in a proper combination.

As an example of the isolation and purification procedure, the culture liquor filtrate is adjusted to pH 3 with hydrochloric acid, and then passed through a column of Diaion HP-10. The resin is thoroughly washed with water and eluted with aqueous 50% methanol. Fractions containing K-26 are collected and methanol is distilled off under reduced pressure. Then, the solution is adjusted to pH 7.0 with aqueous 2N sodium hydroxide, and passed through a column of Diaion HPA-10 ($Cl^-$) (anion exchange resin made by Mitsubishi Kasei Kogyo Co., Ltd. Japan). The resin is thoroughly washed with water and eluted with aqueous 1M sodium chloride. Fractions containing K-26 are collected and adjusted to pH 3 with 2N hydrochloric acid, and passed through a column of Diasion HP-10. The resin is thoroughly washed with water, and eluted with aqueous 50% methanol. Fractions containing K-26 are collected and concentrated under reduced pressure, and freeze-dried, whereby a crude powder is obtained. The crude powder is adequately admixed with cellulose powder, and the resulting mixture is placed on a column of cellulose which is suspended in aqueous 70% isopropanol in advance. Elution is carried out with aqueous 70% isopropanol. Fractions containing K-26 are collected, concentrated under reduced pressure and then freeze-dried. The freeze-dried preparation is dissolved in 0.15M phosphate buffer (pH 7.5) and placed on a column of DEAE-Sephadex A-25 packed using the same buffer as above. Elution is carried out with the same buffer. Fractions containing K-26 are collected, adjusted to pH 3 with 2N hydrochloric acid and passed through a column of Diaion HP-10. The resin is thoroughly washed with water and eluted with aqueous 50% methanol. The eluate is concentrated under reduced pressure and freeze-dried, whereby a partially purified powder is obtained. The thus obtained preparation is further purified by Sephadex LH-20 column chromatography (developing solvent: aqueous 50% methanol). Fractions containing K-26 are collected, concentrated under reduced pressure, and then freeze-dried. The dried preparation is then admixed with silica gel, and the resulting mixture is placed on a column of silica gel packed using the upper layer of n-:butanol:n-propanol:water (2:1:3), and eluted with the same solvent. Fractions containing K-26 are collected and concentrated under reduced pressure to dryness. The residue is dissolved in a small amount of water to remove the insoluble materials, and then freeze-dried, whereby a white powder of K-26 is obtained. In the foregoing purification process, K-26 is detected by Rydon-Smith or iodine reaction. The physical and chemical properties of the thus obtained purified product are as follows.

Physical and chemical properties of K-26:
State: amorphous white powder. Its aqueous solution is acidic.
Melting point: no distinct melting point is exhibited up to 300° C. at which point it turns brown.
Specific rotation: $[\alpha]_D^{20} = -4.8°$ (c=0.1, $H_2O$)
Solubility: readily soluble in alkaline water; soluble in water; sparingly soluble in methanol and ethanol, and insoluble in ethyl acetate, chloroform, hexane, etc.

Color reaction: positive to each of Rydon-Smith and iodine reactions and negative to each of anthrone, aniline, diphenylamine, Ehrlich and nitroprusside reactions.

Constituent amino acids:
K-26 is hydrolyzed in 6N hydrochloric acid at 105° C. for 16 hours and the resulting mixture is analyzed by an amino acid automatic analyzer, whereby isoleucine, tyrosine and an unidentified ninhydrin reaction-positive substance are detected.

Separately, a solution of K-26 in 20% hydrochloric acid is stirred at 110° C. for 21 hours and then concentrated under reduced pressure. The residue is chromatographed on a column of silica gel (developing solvent: isopropanol:chloroform:concentrated aqueous ammonia=3:1:2) to give isoleucine, tyrosine and the aforesaid ninhydrin reaction-positive substance.

The absolute configurations of the isoleucine and tyrosine thus obtained are determined as follows according to the method reported in M. Hasegawa et al., Analytical Biochemistry, 63, 308 (1975).

(1) The isoleucine thus obtained is reacted with l-menthol in the presence of dried hydrogen chloride to form an l-mentyl ester, which is treated with trifluoroacetic acid to protect the amino group with a trifluoroacetyl group and analyzed by gas chromatography.

The above procedure is repeated using authentic samples of DL-isoleucine and L-isoleucine. As a result, the isoleucine from K-26 is identified as L-isoleucine.

(2) The tyrosine thus obtained is converted to an N-trifluoroacetyl-l-menthyl ester thereof in the same manner as described in the above item (1).

The ester is treated with bis-trimethylsilyltrifluoroacetamide to protect the phenolic hydroxyl group with a trimethylsilyl group and analyzed by gas chromatography. The above procedure is repeated using authentic DL-tyrosine and L-tyrosine. As a result, the tyrosine from K-26 is identified as L-tyrosine.

(3) The unidentified ninhydrin reaction-positive substance thus obtained is determined to be (−)-1-amino-2-(4-hydroxyphenyl)ethylphosphonic acid (hereinafter referred to as tyrosine-P) based on its $^1$HNMR, $^{13}$CNMR, $^{31}$PNMR, mass spectrum and specific rotation.

Terminal amino acid analysis: Tyrosine-P is detected by
C-terminal analysis according to the hydrazine decomposition procedure. No N-terminal amino acid is detected by N-terminal analysis according to DNP formation procedure.

Figure 2:
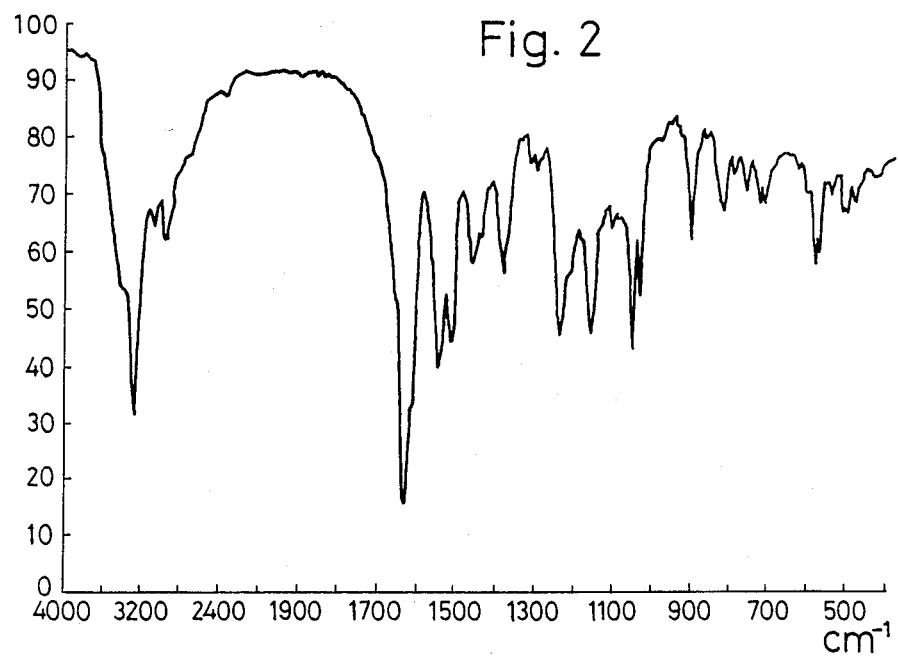
FIG. 2 is the infrared absorption spectrum of K-26.
Figure 3:
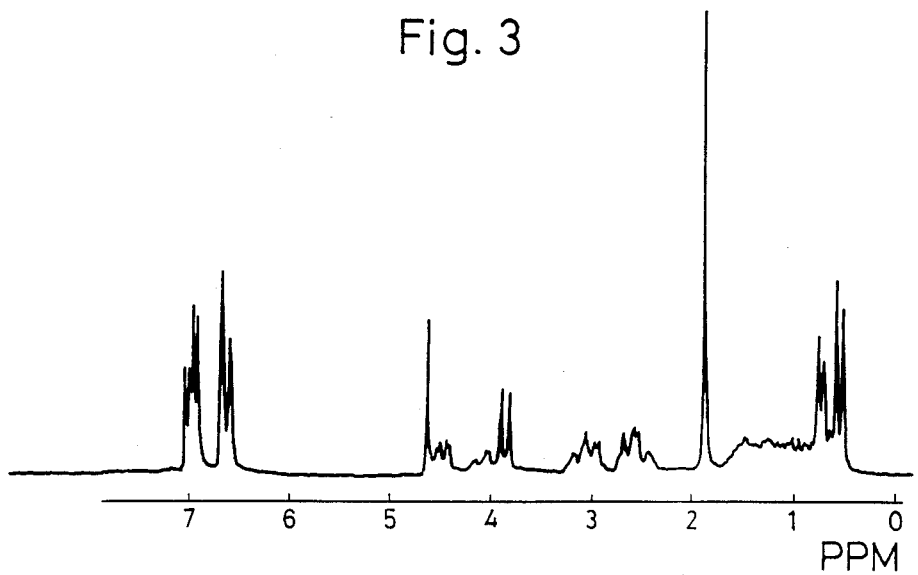
FIG. 3 is the PMR spectrum of K-26 (measured in heavy water)
Figure 4:
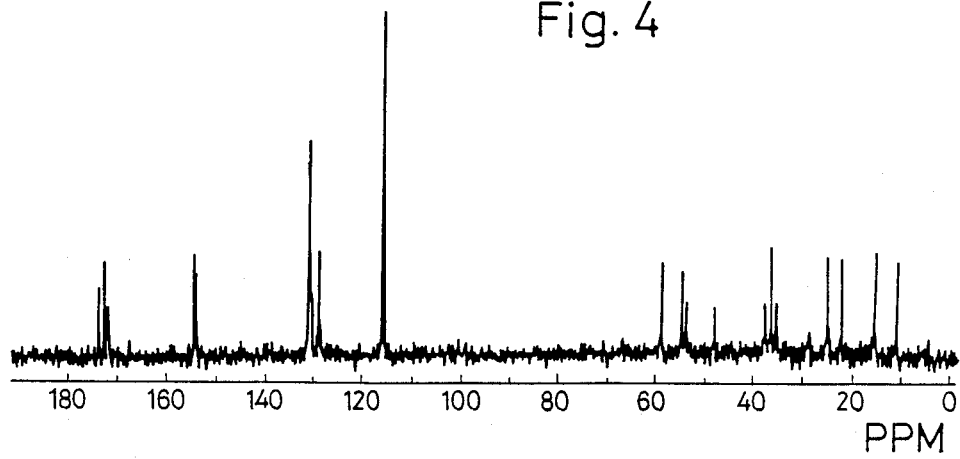
FIG. 4 is the CMR spectrum of K-26.

Additional analysis of K-26 show:
Ultraviolet absorption spectrum: As is illustrated in FIG. 1.
$\lambda_{max}^{H2O} = 278$ nm ($E_1\ _{cm}^{1\%} = 46$). 281 nm ($E_1\ _{cm}^{1\%} = 42$, sh).
(1) neutral and (2) acidic $\lambda_{max}^{H2O} = 294$ nm ($E_1\ _{cm}^{1\%} = 56.5$).
(3) alkaline
Infrared absorption specturm (KBr): As is illustrated in FIG. 2.
PMR spectrum ($D_2O$): As is illustrated in FIG. 3.
CMR spectrum: As is illustrated in FIG. 4 (measured at pD 4.0)
Mass spectrum: Mass spectrum of the hexatrimethylsilyl derivative obtained by treating K-26 with bistrimethylsilyl-trifluoroacetamide and pyridine shows $M^+ = m/Z$ 967.

From the foregoing physical and chemical properties, the structure of K-26 is determined to be:

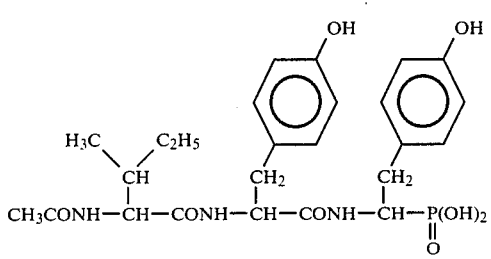

wherein the configuration of the isoleucine and tyrosine parts is L-form and the tyrosine-P part has negative specific rotation.

The Rf values of K-26 on thin layer chromatography by various developing solvents are shown in Tables 1 and 2, where the detection is carried out according to Rydon-Smith reaction.

TABLE 1

| Cellulose thin layer chromatography of K-26 | |
|---|---|
| Developing solvent | Rf value |
| 1. aqueous 70% isopropanol | 0.92 |
| 2. n-butanol:acetic acid:water = 3:1:1 (V/V) | 0.85 |
| 3. Water-saturated n-butanol | 0.57 |

Thin layer: Abicel SF (made by Funakoshi Yakuhin Co., Ltd., Japan).

Development: room temperature, ascending method, 5 hours.

TABLE 2

| Silica gel thin layer chromatography of K-26 | |
|---|---|
| Developing solvent | Rf value |
| 1. n-butanol:acetic acid:water = 4:1:1 (V/V) | 0.52 |
| 2. n-butanol:n-propanol:water = 2:1:3 (V/V), upper layer | 0.45 |
| 3. n-butanol:ethyl acetate:acetic acid:water = 1:1:1:1 (V/V) | 0.72 |
| 4. ethyl acetate | 0 |
| 5. ethyl acetate:methanol = 1:1 (V/V) | 0.1–0.48 |
| 6. methanol | 0.7 |
| 7. chloroform:methanol = 1:1 (V/V) | 0 |

Thin layer: Kieselgel 60 (made by Merck & Co., Inc., U.S.A.).

Development: Room temperature, ascending method, 5 hours for solvents 1–3 and 1.5 hours for solvents 4–7.

The following experiments were carried out to illustrate the hypotensive activity and acute toxicity of K-26.

EXPERIMENT 1

Assessment of hypotensive activity in rats implanted with a catheter:

This experiment is carried out according to the procedure described in "Evaluation of pharmacological effect (1), pharmacological test procedure (II) (Basic Lectures on Development of Drugs V)" compiled by Kyosuke Tsuda et al. and published by Chibun Shokan Publishing Co., on Oct. 10, 1971, pages 464–468.

As test animals, three male spontaneously hypertensive rats (SHR) (weight: 300–400 g) are employed in each group. The rats are intraperitoneally anesthetized with 600 mg/kg of urethane and 60 mg/kg of α-chloralose. The trachea is cannulated, and the blood pressure is recorded on an ink oscillograph through a pressure transducer (Nihon Koden MPU-0.5 made by Nihon Koden Co., Ltd.) from a polyethylene cannula inserted in a left common carotid artery.

The test compound is dissolved in physiological saline solution to yield a dosage of 0.1 l ml/100 g, and intravenously administered through a cannula inserted in a left fermoral vein, and the alteration of blood pressure is measured.

Changes in mean blood pressure are shown in Table 3. The mean blood pressure of 3 rats just before the administration is 143.5±21.3 mm Hg (average value±standard error).

TABLE 3

| Sample | Dosage (mg/kg, iv) | Before administration | Blood pressure change after administration (mm Hg) | | | |
|---|---|---|---|---|---|---|
| | | | 10 min. | 30 min. | 60 min. | 120 min. |
| K-26 | 10 | 0 | −14 | −20 | −30 | +8 |
| " | 30 | 0 | −50 | −50 | −53 | −22 |

It is evident from the foregoing results that K-26 exhibits significant hypotensive activity.

EXPERIMENT 2

In this experiment three dd-strain mice weighing 25±1 g are used in each group. K-26 is dissolved in water at a concentration of 15 mg/ml and one ml of the solution is intravenously administered to the mouse (600 mg/kg administration). Three days after the administration, no deaths are observed in either the K-26 administered group or a control, water administered group.

Because of the foregoing experimental data evidencing that K-26 has hypotensive activity and is of low toxicity, the composition may be used as an hypotensive agent.

In view of the hypotensive activity, K-26 may be used in various formulations for administration. Pharmaceutical compositions of the present invention are prepared by uniformly mixing an effective amount of K-26 with pharmacologically accepatable excipient(s). According to formulations suitable for administration, the excipient may take various forms. It is preferred that the pharmaceutical compositions are administered by injection.

In preparation of the compositions for injection, K-26 is dissolved in water. Alternatively, K-26 may be dissolved in an alkaline solution such as 0.1N aqueous sodium hydroxide, and the solution adjusted to a suitable pH with an acid such as 0.1N hydrochloric acid and diluted with water to a defined volume to prepare an injection. Solubilizing agent(s) may also be used in preparation of an injection. Such solubilizing agents include surfactants such as hydrogenated polyoxyethylene castor oil; injectable solvents such as propylene glycol, N,N-dimethylacetamide and ethanol. Based upon the experimental data, it may be expected that K-26 may be utilized as an hypotensive agent in humans. For such purposes, the active ingredient would be administered by injection in a dose of 0.6–2.5 mg per day for an adult patient (body weight: 50 kg).

Certain specific embodiments of the invention are illustrated by the following representative examples. The following examples as well as the foregoing experiments reflect actual experimental data.

EXAMPLE 1

In this example, Actinomycetes K-26 (FERM-P 5889, NRRL 12379) was used as the seed strain. As a first seed medium, a medium containing 1 g/dl glucose, 1 g/dl soluble starch, 0.3 g/dl beef extract, 0.5 g/dl yeast extract, 0.5 g/dl bactotryptone, and 0.2 g/dl calcium carbonate (pH 7.2 before sterilization) was used. One loopful of the seed strain was inoculated into 14 ml of the seed medium in a 50 ml-large test tube, and cultured with shaking at 30° C. for 11 days. Fourteen milliliters of the seed culture liquor was then added to 300 ml of a second seed medium in a 2 l-Erlenmeyer flask having baffles. The composition of the second seed medium was the same as that of the first seed medium. The second seed culturing was carried out at 30° C. for 4 days. Three hundred milliliters of the second seed culture liquor was then added to 2.7 l of a third seed medium in a 5 l-gar fermenter. The composition of the third seed medium was the same as that of the first seed medium. Seed culturing in the 5 l-jar fermenter was carried out at 30° C. for 2 days with aeration (3 l/min) and agitation (300 r.p.m.). Two liters of the third seed culture liquor was then added to 16 l of a main fermentation medium in a 30 l-stainless steel jar fermenter. The main fermentation medium contained 4 g/dl soluble starch, 3 g/dl soy bean meal, 0.5 g/dl corn steep liquor, 0.05 g/dl dipotassium hydrogen phosphate, 0.05 g/dl magnesium sulfate (heptahydrate), 0.03 g/dl potassium chloride, and 0.3 g/dl calcium carbonate (pH 7.8 before sterilization). The main fermentation was carried out at 30° C. for 5 days with aeration (18 l/min) and agitation (350 r.p.m.).

Thirty-five liters of the thus obtained fermentation liquor (volume corresponding to two 30 l-jar fermenters) was adjusted to pH 3.0 with concentrated sulfuric acid, and admixed with about 1.5 kg of Radiolite No. 600 (made by Showa Kagaku Kogyo Co., Ltd. Japan) as a filter aid, and the cell bodies were filtered off. Thirty-five liters of the resulting filtrate was passed through a column packed with 2 l of Diaion HP-10. The column was washed with 15 l of water, and eluted with 12 l of aqueous 50% methanol. The first 2 l of the eluate was discarded, while the remaining 10 l was collected, concentrated to 5 l under reduced pressure and adjusted to pH 7.0 with aqueous 2N sodium hydroxide. Then, the solution was passed through a column packed with 500 ml of Diaion HPA-10 (Cl−). The column was washed with 3 l of water and then eluted with 3 l of aqueous 1M sodium chloride. All the eluates were collected and adjusted to pH 3.0 with 2N hydrochloric acid. Then, the solution was passed through a column of 500 ml of Diaion HP-10. The column was washed with 3 l of water and eluted with 3 l of aqueous 50% methanol. The first 500 ml of the eluate was discarded, while the remaining 2.5 l was collected, concentrated to about 1 l under reduced pressured and freeze-dried, whereby about 20 g of crude powder of K-26 was obtained. The crude powder was thoroughly admixed with 20 g of cellulose powder (Abicel, made by Funakoshi Yakuhin Co., Ltd. Japan), and the resulting mixture was placed on a column of 1 l of cellulose (Abicel; aqueous 70% isopropanol) and eluted with aqueous 70% isopropanol. The eluate was taken in 18 ml fractions, and K-26 was eluted under fraction Nos. 34–66. The active fractions were collected, concentrated to about 100 ml under reduced pressure and freeze-dried. The freeze-dried preparation was dissolved in 0.15M phosphate buffer (pH 7.5) and placed on a column of 1 l of DEAE-Sephadex A-25 equilibrated with the same buffer. Elution was carried out with the same buffer. The eluate was taken in 18 ml fractions, and K-26 was eluted under fraction Nos. 83–126. The active fractions were collected, adjusted to pH 3.0 with 6N hydrochloric acid, and then passed through a column of 200 ml of Diaion HP-10. The column was washed with 1 l of water and elution was carried out with 1 l of aqueous 50% methanol. All the eluates were collected, concentrated to about 100 ml under reduced pressure and freeze-dried, whereby 450 mg of partially purified powder of K-26 was obtained. Then, the powder was dissolved in 5 ml of aqueous 50% methanol and further purified by Sephadex LH-20 column chromatography (aqueous 50% methanol, column size: 2.3 cm×90 cm). The eluate was taken in 4 ml fractions, and K-26 was eluted under fraction Nos. 45–68. The active fractions were collected, concentrated to about 20 ml under reduced pressure and then freeze-dried. The dried preparation was adequately admixed with 1.5 g of silica gel (Wako gel C-200 made by Wako Junyaku Co., Ltd.), and the resulting mixture was placed on a column of silica gel suspended in the upper layer of n-butanol:n-propanol:water=2:1:3 (Wako gel C-200, column size: 2.1 cm×90 cm), and eluted with the same solvent. The eluate was taken in 3 ml fractions, and K-26 was eluted under fraction Nos. 30–55. The active fractions were collected and concentrated to dryness under reduced pressure. The residue was dissolved in 10 ml of water to remove the insoluble materials and then the solution was freeze-dried, whereby 15 mg of white powder of K-26 was obtained. In the foregoing purification process, detection of K-26 was carried out by means of Rydon-Smith or iodine reaction.

EXAMPLE 2

In this example, 100 mg of K-26 was dissolved in water and the solution was diluted to a volume of 100 ml. The solution was filtered under sterile conditions with a membrane filter. Then, 2.5 ml portions of the filtrate was poured in ampules. The ampules were sealed and sterilized at 121° C. for 20 minutes with high pressure steam to prepare a form of the active compound suitable for injection.

EXAMPLE 3

In this example, 100 mg of K-26 was dissolved in 0.1N aqueous sodium hydroxide, and the solution was adjusted to pH 9 with hydrochloric acid and diluted to a volume of 20 ml with water. Thereafter, the same procedure as described in Example 2 was repeated to prepare an injection containing 2.5 mg of K-26 per ampule (0.5 ml).

What is claimed is:

1. The compound, K-26, represented by the formula:

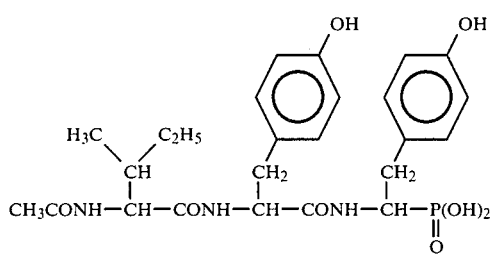

wherein the configuration of the isoleucine and tyrosine parts is L-form and the 1-amino-2-(4-hydroxyphenyl)ethylphosphonic acid part has negative specific rotation.

2. A hypotensive pharmaceutical composition which comprises an effective amount of the compound of claim 1 and at least one pharmacologically acceptable excipient.

3. A method for treating hypertension which comprises administering an effective hypotensive amount of the compound of claim 1 to a hypertensive patient.

* * * * *

UNITED STATES PATENT AND TRADEMARK OFFICE
CERTIFICATE OF CORRECTION

PATENT NO. : 4,683,220

DATED : July 28, 1987

INVENTOR(S) : MASAYUKI YAMATO, ET AL.

It is certified that error appears in the above-identified patent and that said Letters Patent is hereby corrected as shown below:

Title Page, at [54], line 2, "SUBSTANCES K-26," should read --SUBSTANCE K-26,--.

Column 1, line 3, "SUBSTANCES K-26," should read --SUBSTANCE K-26,--.

Column 8, line 6, "0.1 1 ml/100 g," should read --0.1 ml/100 g,--.

Column 8, line 8, "fermoral" should read --femoral--.

Column 9, line 19, "5 1-gar" should read --5 1-jar--.

Signed and Sealed this

Fifteenth Day of March, 1988

Attest:

DONALD J. QUIGG

*Attesting Officer*  *Commissioner of Patents and Trademarks*